(12) United States Patent
Lois

(10) Patent No.: US 8,685,741 B1
(45) Date of Patent: Apr. 1, 2014

(54) METHODS FOR DIAGNOSING IRRITABLE BOWEL SYNDROME

(75) Inventor: Augusto Lois, San Diego, CA (US)

(73) Assignee: Nestec S.A. (CH)

( * ) Notice: Subject to any disclaimer, the term of this patent is extended or adjusted under 35 U.S.C. 154(b) by 855 days.

(21) Appl. No.: 12/043,082

(22) Filed: Mar. 5, 2008

Related U.S. Application Data

(60) Provisional application No. 60/893,594, filed on Mar. 7, 2007.

(51) Int. Cl.
*C07K 16/00* (2006.01)
*A61K 39/395* (2006.01)

(52) U.S. Cl.
USPC ............ 436/86; 435/7.1; 435/6.11; 435/69.6; 424/158.1

(58) Field of Classification Search
USPC ............... 436/86; 435/7, 6.1, 69.6; 424/158.1
See application file for complete search history.

(56) References Cited

U.S. PATENT DOCUMENTS

| | | | |
|---|---|---|---|
| 5,750,355 | A | 5/1998 | Targan et al. |
| 5,916,748 | A | 6/1999 | Targan et al. |
| 5,932,429 | A | 8/1999 | Targan et al. |
| 6,033,864 | A | 3/2000 | Braun et al. |
| 6,074,835 | A | 6/2000 | Braun et al. |
| 6,218,129 | B1 | 4/2001 | Walsh et al. |
| 6,309,643 | B1 | 10/2001 | Braun et al. |
| 2004/0043931 | A1 | 3/2004 | Hersberg et al. |
| 2004/0242972 | A1 | 12/2004 | Adak et al. |
| 2005/0054021 | A1 | 3/2005 | Targan et al. |
| 2005/0164929 | A1 | 7/2005 | Alvarez et al. |
| 2008/0085524 | A1 | 4/2008 | Lois |
| 2008/0166719 | A1 | 7/2008 | Lois |
| 2008/0241163 | A1* | 10/2008 | Burkly et al. .............. 424/158.1 |
| 2010/0094560 | A1 | 4/2010 | Lois et al. |

FOREIGN PATENT DOCUMENTS

| | | |
|---|---|---|
| WO | WO 98/37415 | 8/1998 |
| WO | WO 01/89361 A2 | 11/2001 |
| WO | WO 03/053220 A2 | 7/2003 |
| WO | WO 2004/037073 A2 | 5/2004 |
| WO | WO 2004/048600 A2 | 6/2004 |

OTHER PUBLICATIONS

Campbell, S. et al. The Role of TWEAK/Fn14 in the Pathogenesis of Inflammation and Systemic Autoimmunity.(2004). Fronteirs in Bioscience 9: 2273-2284.*

Dinan, T. et al. Hypothalamic-Pituitary-Gu Axis Dysregulation in Irritable Bowel Syndrome: Plasma Cytokines as a Potential Biomarker.(2006). Gastroenterology. 130: 304-311.*

(Continued)

*Primary Examiner* — Krishnan S Menon
*Assistant Examiner* — Rebecca M Fritchman
(74) *Attorney, Agent, or Firm* — Kilpatrick Townsend & Stockton LLP

(57) ABSTRACT

The present invention provides methods for accurately classifying whether a sample from an individual is associated with an intestinal disorder. In particular, the present invention is useful for associating a sample from an individual as an IBS sample or as a non-IBS sample. The present invention is also useful for ruling out one or more diseases or disorders that present with IBS-like symptoms and ruling in IBS using statistical algorithms and/or empirical data. Thus, the present invention provides an accurate diagnostic prediction of an intestinal disorder and prognostic information useful for guiding treatment decisions.

21 Claims, 1 Drawing Sheet

(56) References Cited

OTHER PUBLICATIONS

Nakamura, R.M., et al.,; "Advances in clinical laboratory tests for inflammatory bowel disease;" *Clinica Chimica Acta* (2003), vol. 335, pp. 9-20.

Reumaux, Dominque; Best Practice and Research Clinical Gastroenterology; Serological Markers in Inflammatory Bowel Disease; Feb. 2003; vol. 17(1); pp. 19-35.

Dubinsky, Maria C.; Clinical Utility of Serodiagnostic Testing in Suspect Pediatric Inflammatory Bowel Disease; The American Journal of Gastroenterology; vol. 96(3); 2001; pp. 758-765.

Talley, N.J., "Irritable Bowel Syndrome," Intern Med J, Nov. 2006, 23(11): 724.728.

Wiley, S.R. et al., "TWEAK, a Member of the TNF Superfamily, is a Multifunctional Cytokine That Binds the TweakR/Fn14 Receptor," *Cytokine & Growth Factor Reviews*, Jan. 1, 2003, vol. 14, pp. 241-249.

* cited by examiner

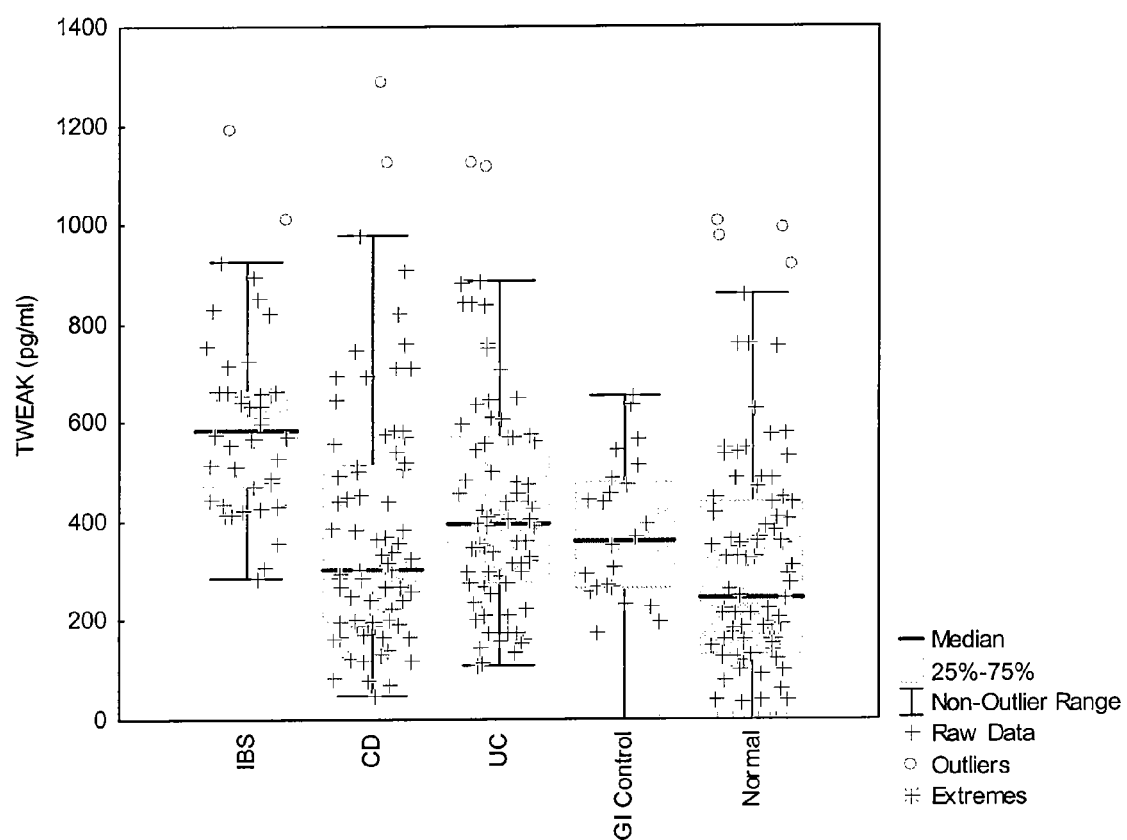

METHODS FOR DIAGNOSING IRRITABLE BOWEL SYNDROME

CROSS-REFERENCES TO RELATED APPLICATIONS

This application claims priority to U.S. Provisional Application No. 60/893,594, filed Mar. 7, 2007, the disclosure of which is hereby incorporated by reference in its entirety for all purposes.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Irritable bowel syndrome (IBS) is the most common of all gastrointestinal disorders, affecting 10-20% of the general population and accounting for more than 50% of all patients with digestive complaints. However, studies suggest that only about 10% to 50% of those afflicted with IBS actually seek medical attention. Patients with IBS present with disparate symptoms such as, for example, abdominal pain predominantly related to defecation, diarrhea, constipation or alternating diarrhea and constipation, abdominal distention, gas, and excessive mucus in the stool. More than 40% of IBS patients have symptoms so severe that they have to take time off from work, curtail their social life, avoid sexual intercourse, cancel appointments, stop traveling, take medication, and even stay confined to their house for fear of embarrassment. The estimated health care cost of IBS in the United States is $8 billion per year (see, Talley et al., Gastroenterol., 109, 1736-1741 (1995)).

The precise pathophysiology of IBS is not well understood. Nevertheless, there is a heightened sensitivity to visceral pain perception, known as peripheral sensitization. This sensitization involves a reduction in the threshold and an increase in the gain of the transduction processes of primary afferent neurons, attributable to a variety of mediators including monoamines (e.g., catecholamines and indoleamines), substance P, and a variety of cytokines and prostanoids such as E-type prostaglandins (see, e.g., Mayer et al., Gastroenterol., 107:271-293 (1994)). Also implicated in the etiopathology of IBS is intestinal motor dysfunction, which leads to abnormal handling of intraluminal contents and/or gas (see, e.g., Kellow et al., Gastroenterol., 92:1885-1893 (1987); Levitt et al., Ann. Int. Med, 124:422-424 (1996)). Psychological factors may also contribute to IBS symptoms appearing in conjunction with, if not triggered by, disturbances including depression and anxiety (see, e.g., Drossman et al., Gastroenterol. Int., 8:47-90 (1995)).

The causes of IBS are not well understood. The walls of the intestines are lined with layers of muscle that contract and relax as they move food from the stomach through the intestinal tract to the rectum. Normally, these muscles contract and relax in a coordinated rhythm. In IBS patients, these contractions are typically stronger and last longer than normal. As a result, food is forced through the intestines more quickly in some cases causing gas, bloating, and diarrhea. In other cases, the opposite occurs: food passage slows and stools become hard and dry causing constipation.

Inflammatory bowel disease (IBD) is a heterogeneous group of diseases that have a common manifestation of (gut) mucosal inflammation. In general, IBD encompasses two major forms of intestinal inflammation: ulcerative colitis and Crohn's disease, which is also known also as Crohn's ileitis, regional enteritis, or granulomatous colitis. Estimates place the domestic prevalence of these conditions between one and two million patients, with similar rates in other northern European countries (see, Crohn's & Colitis Foundation of America 1/99 Update). The clinical and histopathologic features of IBD are well characterized; however, the etiology and pathogenesis of IBD are still subjects of intense research. Currently, a variety of medical treatment modalities are used, with moderate success, to both control active "flare-ups" of IBD as well as to maintain remission(s). Aminosalicylate preparations such as sulfasalazine and mesalamine are the most common anti-inflammatory agents which are used to control ulcerative colitis and, to a lesser extent, Crohn's disease. While the specific mechanism remains undefined, inhibition of eicosanoid mediators such as prostaglandins and thromboxanes is the probable mechanism of action (see, Stein et al., Gastroent. Clin. N Amer., 28:297-321 (1999)). Other typical treatments include corticosteroids and antibiotics such as metronidazole and ciprofloxacin for acute flares of disease. The other large category of drugs used in IBD is the immunomodulators, including azathioprine, methotrexate, and cyclosporine, the efficacy of which are principally related to their ability to inhibit T-cell related immune response and inflammatory cytokine cascades (see, Stotland et al., *Primary Care*, 23:577-608 (1996)). These treatments, unfortunately, induce worrisome side effects.

As mentioned, the causes of IBD remain obscure. A currently accepted hypothesis is that IBD represents an interaction between genetic and environmental factors, and implicates T-cell dysregulation, specifically an abnormally severe T-cell inflammatory response to mucosal antigens. Commensal gut flora is implicated as the source of such antigens. Regardless of the initial insult that activates the immune system, the inflammatory cascade which follows has been characterized. The $T_h$ cell cytokines IL-1 and TNF-α are considered to be central to the pathogenesis of IBD (see, Papadakis et al., Gastroent. Clin. N. Amer., 28:283-296 (1999)). Further down the inflammatory cascade are the eicosanoid products of arachidonic acid, particularly Prostaglandin E2 ($PGE_2$) and Leukotriene B4 ($LTB_4$), which have been found in high levels in IBD patients (see, Stotland et al., supra).

Because the symptoms of IBS are similar or identical to the symptoms of so many other intestinal illnesses, it can take years before a correct diagnosis is made. For example, patients who have IBD, but who exhibit mild signs and symptoms such as bloating, diarrhea, constipation, and abdominal pain, may be difficult to distinguish from patients with IBS. As a result, the similarity in symptoms between IBS and IBD renders rapid and accurate diagnosis difficult. The difficulty in differentially diagnosing IBS and IBD hampers early and effective treatment of these diseases. Unfortunately, rapid and accurate diagnostic methods for definitively distinguishing IBS from other intestinal diseases or disorders presenting with similar symptoms are currently not available. The present invention satisfies this need and provides related advantages as well.

BRIEF SUMMARY OF THE INVENTION

The present invention provides methods for accurately classifying whether a sample from an individual is associated with an intestinal disorder. As such, in one embodiment, the present invention provides a method for classifying whether a sample from an individual is associated with an intestinal disorder (e.g., IBS), comprising:

(a) determining the presence or level of TWEAK in the sample; and (b) associating the sample with an intestinal disorder based upon the presence or level of TWEAK.

In another embodiment, the present invention provides a method for monitoring the progression or regression of an intestinal disorder (e.g., IBS) in an individual, comprising:

(a) determining the presence or level of TWEAK in a sample from the individual; and (b) determining the presence or severity of the intestinal disorder in the individual based upon the presence of TWEAK.

In still another embodiment, the present invention provides a method for monitoring drug efficacy in an individual receiving a drug useful for treating an intestinal disorder (e.g., IBS), comprising:

(a) determining the presence or level of TWEAK in a first sample from the individual prior to drug treatment;

(b) determining the presence or level of TWEAK in a second sample from the individual after drug treatment has begun; and (c) determining the effectiveness of the drug based upon the presence or level of TWEAK in the first and second samples.

Other objects, features, and advantages of the present invention will be apparent to one of skill in the art from the following detailed description and FIGURE.

BRIEF DESCRIPTION OF THE DRAWINGS

FIG. 1 illustrates a quartile analysis of TWEAK levels in IBS and non-IBS patient samples.

DETAILED DESCRIPTION OF THE INVENTION

I. Introduction

Diagnosing a patient as having an intestinal disorder can be challenging due to the similarity in symptoms between the diseases and disorders. For example, patients who have inflammatory bowel disease (IBD), but who exhibit mild signs and symptoms such as bloating, diarrhea, constipation, and abdominal pain can be difficult to distinguish from patients with irritable bowel syndrome (IBS). As a result, the similarity in symptoms between IBS and IBD renders rapid and accurate diagnosis difficult and hampers early and effective treatment of the disease.

II. Definitions

As used herein, the following terms have the meanings ascribed to them unless specified otherwise.

The term "classifying" includes "to associate" or "to categorize" a sample with a disease state. In certain instances, "classifying" is based on empirical data (presence or absence of TWEAK and/or level of TWEAK), statistical evidence, or both. In certain embodiments, the methods of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "irritable bowel syndrome" or "IBS" includes a group of functional bowel disorders characterized by one or more symptoms including abdominal pain, abdominal discomfort, change in bowel pattern, loose or more frequent bowel movements, diarrhea, and constipation, typically in the absence of any apparent structural abnormality. There are at least three forms of IBS, depending on which symptom predominates: (1) diarrhea-predominant (IBS-D); (2) constipation-predominant (IBS-C); and (3) IBS with alternating stool pattern (IBS-A). IBS can also occur in the form of a mixture of symptoms (IBS-M). There are also various clinical subtypes of IBS, such as post-infectious IBS (IBS-PI).

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.*, 11:267-286 (1997)). One skilled in the art will appreciate that samples such as serum samples can be diluted prior to the analysis of TWEAK levels.

The term "individual," "subject," or "patient" typically refers to humans, but also to other animals including, e.g., other primates, rodents, canines, felines, equines, ovines, porcines, and the like.

The term "monitoring the progression or regression of an intestinal disorder" includes the use of the methods of the present invention to determine the disease state (e.g., presence or severity of IBS) of an individual. In certain instances, the results of an algorithm (e.g., a learning statistical classifier system) are compared to those results obtained for the same individual at an earlier time. In some aspects, the methods of the present invention can also be used to predict the progression of an intestinal disorder (e.g., IBS) by determining the likelihood for the disorder to progress either rapidly or slowly in an individual based on the presence or level of TWEAK in a sample. In other aspects, the methods of the present invention can also be used to predict the regression of an intestinal disorder (e.g., IBS) by determining the likelihood for the intestinal disorder to regress either rapidly or slowly in an individual based on the presence or level of TWEAK in a sample.

The term "monitoring drug efficacy in an individual receiving a drug useful for treating an intestinal disorder" includes the use of the methods of the present invention to determine the disease state (e.g., presence or severity of IBS) of an individual after a therapeutic agent for treatment. In certain instances, the results of an algorithm (e.g., a learning statistical classifier system) are compared to those results obtained for the same individual before initiation of use of the therapeutic agent or at an earlier time in therapy. As used herein, a drug useful for treating an intestinal disorder (e.g., IBS) is any compound or drug used to improve the health of the individual and includes, without limitation, serotonergic agents, antidepressants, chloride channel activators, chloride channel blockers, guanylate cyclase agonists, antibiotics, opioids, neurokinin antagonists, antispasmodic or anticholinergic agents, belladonna alkaloids, barbiturates, glucagon-like peptide-1 (GLP-1) analogs, corticotropin releasing factor (CRF) antagonists, probiotics, free bases thereof, pharmaceutically acceptable salts thereof, derivatives thereof, analogs thereof, and combinations thereof.

The term "therapeutically effective amount or dose" includes a dose of a drug that is capable of achieving a therapeutic effect in a subject in need thereof. For example, a therapeutically effective amount of a drug useful for treating an intestinal disorder (e.g., IBS) can be the amount that is capable of preventing or relieving one or more symptoms associated with the intestinal disorder. The exact amount can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

III. Description of the Embodiments

The present invention provides methods for accurately classifying whether a sample from an individual is associated with an intestinal disorder. In some embodiments, the present invention is useful for classifying a sample from an individual as an IBS sample using a statistical algorithm (e.g., a learning statistical classifier system) and/or empirical data (e.g., the presence or level of TWEAK). In certain instances, the present invention is also useful for ruling out one or more diseases or disorders that present with IBS-like symptoms and ruling in IBS using a combination of statistical algorithms (e.g., learning statistical classifier systems) and/or empirical data (e.g., the presence or level of TWEAK). Accordingly, the present invention provides an accurate diagnostic prediction of an intestinal disorder and prognostic information useful for guiding treatment decisions.

In some instances, the present invention provides a method for classifying whether a sample from an individual is associated with an intestinal disorder, the method comprising:
  (a) determining the presence or level of TWEAK in the sample; and
  (b) associating the sample with an intestinal disorder based upon the presence or level of TWEAK.

"TWEAK" or "TNF-related weak inducer of apoptosis" is a member of the TNF superfamily of structurally related cytokines. Full-length, membrane-anchored TWEAK can be found on the surface of many cell types and a smaller, biologically active form, generated via proteolytic processing, has also been detected in the extracellular milieu (see, e.g., Chicheportiche et al., *J. Biol. Chem.*, 272:32401-32410 (1997)). TWEAK acts via binding to a TNF receptor superfamily member named fibroblast growth factor-inducible 14 (Fn14; also known as tumor necrosis factor receptor superfamily member 12A or TNFRSF12A). TWEAK has multiple biological activities, including stimulation of cell growth and angiogenesis, induction of inflammatory cytokines, and stimulation of apoptosis (see, e.g., Wiley et al., *Cytokine Growth Factor Rev.*, 14:241-249 (2003)). In particular, TWEAK has been shown to induce the expression of $PGE_2$, MMP-1, IL-6, IL-8, RANTES, and IP-10 in fibroblasts and synoviocytes, and to upregulate ICAM-1, E-selectin, IL-8, and MCP-1 expression in endothelial cells (see, e.g., Campbell et al., *Front. Biosci.*, 9:2273-2284 (2004)). It has also been demonstrated that TWEAK binding to the Fn14 receptor, or constitutive Fn14 overexpression, activates the NF-κB signaling pathway, which plays an important role in immune and inflammatory processes, oncogenesis, cancer therapy resistance, and tumorigenesis (see, e.g., Winkles et al., *Cancer Lett.*, 235:11-17 (2006); and Winkles et al., *Front. Biosci.*, 12:2761-2771 (2007)). One skilled in the art will appreciate that TWEAK is also known as tumor necrosis factor ligand superfamily member 12 (TNFSF12), APO3 ligand (APO3L), CD255, DR3 ligand, growth factor-inducible 14 (Fn14) ligand, and UNQ181/PRO207.

The human TWEAK polypeptide sequence is set forth in, e.g., Genbank Accession Nos. NP_003800 (SEQ ID NO:1) and AAC51923. The human TWEAK mRNA (coding) sequence is set forth in, e.g., Genbank Accession Nos. NM_003809 (SEQ ID NO:2) and BC104420. The human TWEAK genomic sequence is set forth in, e.g., Genbank Accession Nos. NC_000017.9 and NW_926584.1.

In some embodiments, the presence or level of TWEAK is measured using, for example, an aliquot or dilution of the individual's sample. In certain instances, the level of TWEAK in the individual's sample is considered to be elevated when it is at least about 25%, 50%, 75%, 100%, 125%, 150%, 175%, 200%, 250%, 300%, 350%, 400%, 450%, 500%, 600%, 700%, 800%, 900%, or 1000% greater than the level of TWEAK in a comparative sample (e.g., a normal or GI control sample) or population of samples (e.g., greater than a median level of TWEAK in a comparative population of normal or GI control samples). In certain other instances, the level of TWEAK in the individual's sample is considered to be lowered when it is at least about 5%, 10%, 15%, 20%, 25%, 30%, 35%, 40%, 45%, 50%, 55%, 60%, 65%, 70%, 75%, 80%, 85%, 90%, or 95% less than the level of TWEAK in a comparative sample (e.g., a normal or GI control sample) or population of samples (e.g., less than a median level of TWEAK in a comparative population of a normal or GI control samples).

There are a variety of intestinal disorders that can be classified using the methods of the present invention. For example, the intestinal disorder can be IBS or a non-IBS intestinal disorder. IBS includes, for example, IBS-constipation (IBS-C), IBS-diarrhea (IBS-D), IBS-mixed (IBS-M), IBS-alternating (IBS-A), and post-infectious IBS (IBS-PI). Alternatively, the intestinal disorder can be a non-IBS intestinal disorder. Non-IBS intestinal disorders include, but are not limited to, inflammatory bowel disease (IBD) and non-IBD intestinal disorders. IBD includes, for example, Crohn's disease and ulcerative colitis. In certain instances, the sample from the individual is not associated with an intestinal disorder, i.e., the sample is classified as a normal sample based upon the presence or level of TWEAK.

As a person skilled in the art will appreciate, a variety of structural or metabolic diseases and disorders can cause signs or symptoms that are similar to each other. As non-limiting examples, patients with diseases and disorders such as IBD, Celiac disease (CD), acute inflammation, diverticulitis, ileal pouch-anal anastomosis, microscopic colitis, chronic infectious diarrhea, lactase deficiency, cancer (e.g., colorectal cancer), a mechanical obstruction of the small intestine or colon, an enteric infection, ischemia, maldigestion, malabsorption, endometriosis, and unidentified inflammatory disorders of the intestinal tract can present with abdominal discomfort associated with mild to moderate pain and a change in the consistency and/or frequency of stools that are similar to IBS. Additional IBS-like symptoms can include chronic diarrhea or constipation or an alternating form of each, weight loss, abdominal distention or bloating, and mucus in the stool.

Most IBD patients can be classified into one of two distinct clinical subtypes, Crohn's disease and ulcerative colitis. Crohn's disease is an inflammatory disease affecting the lower part of the ileum and often involving the colon and other regions of the intestinal tract. Ulcerative colitis is characterized by an inflammation localized mostly in the mucosa and submucosa of the large intestine. Patients suffering from these clinical subtypes of IBD typically have IBS-like symptoms such as, for example, abdominal pain, chronic diarrhea, weight loss, and cramping.

In some embodiments, the methods of the present invention can further comprise classifying a sample from an individual as an IBS-constipation (IBS-C), IBS-diarrhea (IBS-D), IBS-mixed (IBS-M), IBS-alternating (IBS-A), or post-infectious IBS (IBS-PI) sample. In certain instances, the methods of the present invention can be used to differentiate an IBS-C sample from an IBS-D sample in an individual previously identified as having IBS. In certain other instances, the methods of the present invention can be used to classify a sample from an individual not previously diagnosed with IBS as an IBS-C sample, IBS-D sample, or non-IBS sample.

In additional embodiments, the methods of the present invention can further comprise ruling out intestinal inflammation. Non-limiting examples of intestinal inflammation include acute inflammation, diverticulitis, ileal pouch-anal anastomosis, microscopic colitis, infectious diarrhea, and combinations thereof. In some instances, the intestinal inflammation is ruled out based upon the presence or level of C-reactive protein (CRP), lactoferrin, calprotectin, or combinations thereof.

The clinical presentation of Celiac disease is also characterized by IBS-like symptoms such as abdominal discomfort associated with chronic diarrhea, weight loss, and abdominal distension. Celiac disease is an immune-mediated disorder of the intestinal mucosa that is typically associated with villous atrophy, crypt hyperplasia, and/or inflammation of the mucosal lining of the small intestine. In addition to the malabsorption of nutrients, individuals with Celiac disease are at risk for mineral deficiency, vitamin deficiency, osteoporosis, autoimmune diseases, and intestinal malignancies (e.g., lymphoma and carcinoma). It is thought that exposure to proteins such as gluten (e.g., glutenin and prolamine proteins which are present in wheat, rye, barley, oats, millet, triticale, spelt, and kamut), in the appropriate genetic and environmental context, is responsible for causing Celiac disease.

Other diseases and disorders characterized by intestinal inflammation that present with IBS-like symptoms that can be distinguished include, for example, acute inflammation, diverticulitis, ileal pouch-anal anastomosis, microscopic colitis, and chronic infectious diarrhea, as well as unidentified inflammatory disorders of the intestinal tract. Patients experiencing episodes of acute inflammation typically have elevated C-reactive protein (CRP) levels in addition to IBS-like symptoms. CRP is produced by the liver during the acute phase of the inflammatory process and is usually released about 24 hours post-commencement of the inflammatory process. Patients suffering from diverticulitis, ileal pouch-anal anastomosis, microscopic colitis, and chronic infectious diarrhea typically have elevated fecal lactoferrin and/or calprotectin levels in addition to IBS-like symptoms. Lactoferrin is a glycoprotein secreted by mucosal membranes and is the major protein in the secondary granules of leukocytes. Leukocytes are commonly recruited to inflammatory sites where they are activated, releasing granule content to the surrounding area. This process increases the concentration of lactoferrin in the stool.

Increased lactoferrin levels are observed in patients with ileal pouch-anal anastomosis (i.e., a pouch is created following complete resection of colon in severe cases of Crohn's disease) when compared to other non-inflammatory conditions of the pouch, like irritable pouch syndrome. Elevated levels of lactoferrin are also observed in patients with diverticulitis, a condition in which bulging pouches (i.e., diverticula) in the digestive tract become inflamed and/or infected, causing severe abdominal pain, fever, nausea, and a marked change in bowel habits. Microscopic colitis is a chronic inflammatory disorder that is also associated with increased fecal lactoferrin levels. Microscopic colitis is characterized by persistent watery diarrhea (non-bloody), abdominal pain usually associated with weight loss, a normal mucosa during colonoscopy and radiological examination, and very specific histopathological changes. Microscopic colitis consists of two diseases, collagenous colitis and lymphocytic colitis. Collagenous colitis is of unknown etiology and is found in patients with long-term watery diarrhea and a normal colonoscopy examination. Both collagenous colitis and lymphocytic colitis are characterized by increased lymphocytes in the lining of the colon. Collagenous colitis is further characterized by a thickening of the sub-epithelial collagen layer of the colon. Chronic infectious diarrhea is an illness that is also associated with increased fecal lactoferrin levels. Chronic infectious diarrhea is usually caused by a bacterial, viral, or protozoan infection, with patients presenting with IBS-like symptoms such as diarrhea and abdominal pain. Increased lactoferrin levels are also observed in patients with IBD.

In addition to determining CRP and/or lactoferrin and/or calprotectin levels, diseases and disorders associated with intestinal inflammation can also be ruled out by detecting the presence of blood in the stool, such as fecal hemoglobin. Intestinal bleeding that occurs without the patient's knowledge is called occult or hidden bleeding. The presence of occult bleeding (e.g., fecal hemoglobin) is typically observed in a stool sample from the patient. Other conditions such as ulcers (e.g., gastric, duodenal), cancer (e.g., stomach cancer, colorectal cancer), and hemorrhoids can also present with IBS-like symptoms including abdominal pain and a change in the consistency and/or frequency of stools.

In addition, fecal calprotectin levels can also be assessed. Calprotectin is a calcium binding protein with antimicrobial activity derived predominantly from neutrophils and monocytes. Calprotectin has been found to have clinical relevance in cystic fibrosis, rheumatoid arthritis, IBD, colorectal cancer, HIV and other inflammatory diseases. Its level has been measured in serum/plasma, oral, cerebrospinal and synovial fluids, in urine and feces. Advantages of fecal calprotectin in GI disorders have been recognized: stable for 3-7 days at room temperature enabling sample shipping through regular mail; correlated to fecal alpha 1-antitrypsin in patients with Crohn's disease; and elevated in a great majority of patients with gastrointestinal carcinomas and IBD. It was found that fecal calprotectin correlates well with endoscopic and histological gradings of disease activity in ulcerative colitis, and with fecal excretion of indium-111-labelled neutrophilic granulocytes, which is a standard of disease activity in IBD.

In view of the foregoing, it is clear that a wide array of diseases and disorders can cause IBS-like symptoms, thereby creating a substantial obstacle for definitively classifying a sample as an IBS sample. In certain instances, the present invention overcomes this limitation by classifying a sample from an individual as being associated with IBS using, for example, a statistical algorithm, or by excluding (i.e., ruling out) those diseases and disorders that share a similar clinical presentation as IBS and identifying (i.e., ruling in) IBS in a sample using, for example, a combination of statistical algorithms.

IV. Measuring TWEAK

The sample used for detecting or determining the presence or level of TWEAK is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention can further comprise obtaining the sample from the individual prior to detecting or determining the presence or level of TWEAK in the sample.

In certain instances, the presence or level of TWEAK is determined using an immunoassay or an immunohistochemical assay. Non-limiting examples of immunoassays suitable for use in the present invention include enzyme-linked immunosorbent assays (ELISA) and electrochemiluminescence immunoassays (ECLIA). Examples of immunohistochemical assays suitable for use in the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

Suitable ELISA kits for determining the presence or level of TWEAK in a biological sample such as a serum, plasma, saliva, or urine sample are available from, e.g., Antigenix America Inc. (Huntington Station, N.Y.), Bender MedSystems Inc. (Burlingame, Calif.), Agdia Inc. (Elkhart, Ind.), American Research Products Inc. (Belmont, Mass.), Biomeda Corp. (Foster City, Calif.), BioVision, Inc. (Mountain View, Calif.), and Kamiya Biomedical Co. (Seattle, Wash.). An ELISA for detecting TWEAK or measuring TWEAK levels can also be performed according to the method described in Kawakita et al., supra, using anti-TWEAK antibodies available from Santa Cruz Biotechnology, Inc. (Santa Cruz, Calif.), PeproTech EC Ltd. (London, UK), or eBioscience (San Diego, Calif.). As a non-limiting example, immunohistochemical staining for the presence or level of TWEAK can be performed on a tissue sample according to the protocol described in Kawakita et al., supra, using commercially available anti-TWEAK antibodies.

Suitable ECLIA kits for determining the presence or level of TWEAK in a biological sample such as a serum, plasma, saliva, or urine sample are available from, e.g., Meso Scale Discovery (Gaithersburg, Md.). In some embodiments, an ECLIA for measuring TWEAK levels is based on multi-array technology and electrochemiluminescent detection. As a non-limiting example, an ECLIA can use microplates with electrodes integrated into the bottom of the plates. A biological sample such as a diluted serum sample can be incubated with the microplates and the antigen of interest (i.e., TWEAK) immobilized to the carbon electrode in the plates by passive adsorption. In certain instances, the ECLIA employs the use of electrochemiluminescent labels covalently attached to antibodies against the antigen (i.e., anti-TWEAK antibodies). Electrochemiluminescent labels generally emit light when electrochemically stimulated. Following a wash step, the detection process can be initiated at electrodes located in the bottom of the microplates. Only labels (i.e., labeled anti-TWEAK antibodies) near the electrode are excited and detected. Absorbance is typically measured at 620 nm.

In certain other instances, the presence or level of TWEAK is determined using an assay such as a hybridization assay or an amplification-based assay. Examples of hybridization assays suitable for use in the present invention include, but are not limited to, Northern blotting, dot blotting, RNase protection, and combinations thereof. Suitable amplification-based assays for use in the present invention include, without limitation, reverse transcriptase-polymerase chain reaction (RT-PCR) assays. For example, the RT-PCR assay described in Kawakita et al., Int. J. Oncol., 26:87-93 (2005) can be performed to detect TWEAK or measure TWEAK levels in a sample using the following primers: TWEAK sense primer, 5'-CCCATGGCCGCCCGTCGGAG-3' (SEQ ID NO:3); and TWEAK antisense primer, 5'-GGGCCAACAGCCCAGA-CACC-3' (SEQ ID NO:4).

One skilled in the art will also appreciate that the presence or level of TWEAK can be determined by Western blot or flow cytometric analysis as described, for example, in Kawakita et al., supra, using commercially available anti-TWEAK antibodies.

V. Statistical Algorithms

In some aspects, the present invention provides methods for classifying whether a sample is associated with an intestinal disorder using a statistical algorithm or process to classify the sample. The sample can be an IBS sample or non-IBS sample. In other aspects, the present invention provides methods for classifying whether a sample is associated with IBS using a first statistical algorithm or process to classify the sample as a non-IBD sample or IBD sample (i.e., IBD rule-out step), followed by a second statistical algorithm or process to classify the non-IBD sample as an IBS sample or non-IBS sample (i.e., IBS rule-in step). Preferably, the statistical algorithms or processes independently comprise one or more learning statistical classifier systems. As described herein, a combination of learning statistical classifier systems advantageously provides improved sensitivity, specificity, negative predictive value, positive predictive value, and/or overall accuracy for classifying whether a sample is associated with IBS.

The term "statistical algorithm" or "statistical process" includes any of a variety of statistical analyses used to determine relationships between variables. In the present invention, the variables are the presence or level of TWEAK. Any number of markers can be analyzed using a statistical algorithm described herein. For example, the presence or levels of 1, 2, 3, 4, 5, 6, 7, 8, 9, 10, 11, 12, 13, 14, 15, 16, 17, 18, 19, 20, 25, 30, 35, 40, 50, or more markers can be included in a statistical algorithm. In one embodiment, logistic regression is used. In another embodiment, linear regression is used. In certain instances, the statistical algorithms of the present invention can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels, etc.) as variables in the algorithms (just as with continuous variables).

Preferably, the statistical algorithms of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, and the like.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the Random Forests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the CART software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

The learning statistical classifier systems described herein can be trained and tested using a cohort of samples (e.g., serological samples) from healthy individuals, IBS patients, IBD patients, Celiac disease patients, and/or patients with other intestinal disorders. For example, samples from patients diagnosed by a physician, and preferably by a gastroenterologist as having IBD using a biopsy, colonoscopy, or an immunoassay as described in, e.g., U.S. Pat. No. 6,218,129, are suitable for use in training and testing the learning statistical classifier systems of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from patients diagnosed with IBS using a published criteria such as the Manning, Rome I, Rome II, or Rome III diagnostic criteria are suitable for use in training and testing the learning statistical classifier systems of the present invention. Samples from healthy individuals can include those that were not identified as IBD and/or IBS samples. One skilled in the art will know of additional techniques and diagnostic criteria for obtaining a cohort of patient samples that can be used in training and testing the learning statistical classifier systems of the present invention.

As used herein, the term "sensitivity" refers to the probability that a method of the present invention gives a positive result when the sample is positive, e.g., having an intestinal disorder such as IBS. Sensitivity is calculated as the number of true positive results divided by the sum of the true positives and false negatives. Sensitivity essentially is a measure of how well a method of the present invention correctly identifies those with an intestinal disorder from those without the disease. The statistical algorithms can be selected such that the sensitivity of classifying the intestinal disorder is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" refers to the probability that a method of the present invention gives a negative result when the sample is not positive, e.g., not having an intestinal disorder such as IBS. Specificity is calculated as the number of true negative results divided by the sum of the true negatives and false positives. Specificity essentially is a measure of how well a method of the present invention excludes those who do not have an intestinal disorder from those who have the disease. The statistical algorithms can be selected such that the specificity of classifying the intestinal disorder is at least about 70%, for example, at least about 75%, 80%, 85%, 86%, 87%, 88%, 89%, 90%, 91%, 92%, 93%, 94%, 95%, 96%, 97%, 98%, or 99%.

As used herein, the term "negative predictive value" or "NPV" refers to the probability that an individual identified as not having an intestinal disorder such as IBS actually does not have the disease. Negative predictive value can be calculated as the number of true negatives divided by the sum of the true negatives and false negatives. Negative predictive value is determined by the characteristics of the method as well as the prevalence of the disease in the population analyzed. The statistical algorithms can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" refers to the probability that an individual identified as having an intestinal disorder such as IBS actually has the disease. Positive predictive value can be calculated as the number of true positives divided by the sum of the true positives and false positives. Positive predictive value is determined by the characteristics of the method as well as the prevalence of the disease in the population analyzed. The statistical algorithms can be selected such that the positive predictive value in a population having a disease prevalence is in the range of about 80% to about 99% and can be, for example, at least about 80%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the methods of the present invention, the statistical algorithms can be selected to produce a desired clinical parameter for a clinical population with a particular prevalence of an intestinal disorder such as IBS. For example, learning statistical classifier systems can be selected for an intestinal disorder prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a method of the present invention classifies a disease state. Overall accuracy is calculated as the sum of the true positives and true negatives divided by the total number of sample results and is affected by the prevalence of the disease in the population analyzed. For example, the statistical algorithms can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, classifying whether a sample is associated with an intestinal disorder is based upon the presence or level of TWEAK in conjunction with a statistical algorithm. In certain instances, the statistical algorithm is a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a NN (e.g., artificial NN, etc.). Additional examples of learning statistical classifier systems suitable for use in the present invention are described in U.S. patent application Ser. Nos. 11/679,149 and 11/838,810.

In certain instances, the statistical algorithm is a single learning statistical classifier system. Preferably, the single learning statistical classifier system comprises a tree-based statistical algorithm such as a RF or C&RT. As a non-limiting example, a single learning statistical classifier system can be used to classify the intestinal disorder based upon a prediction or probability value and the presence or level of TWEAK, alone or in combination with the presence or severity of at least one symptom. The use of a single learning statistical classifier system typically classifies the intestinal disorder with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain other instances, the statistical algorithm is a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the presence or level of TWEAK, alone or in combination with the presence or severity of at least one symptom, and a NN can then be used to classify the intestinal disorder based upon the prediction or probability value and the presence or level of TWEAK. The hybrid RF/NN learning statistical classifier system advantageously classifies the intestinal disorder with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

VI. Therapy and Therapeutic Monitoring

In certain embodiments, the present invention provides a method for monitoring the progression or regression of an intestinal disorder (e.g., IBS) in an individual, comprising:
(a) determining the presence or level of TWEAK in a sample from the individual; and
(b) determining the presence or severity of an intestinal disorder (e.g., IBS) in the individual based upon the presence of TWEAK.

An individual can also be monitored at periodic time intervals to assess the individual's progression or regression based upon the presence or level of TWEAK. In fact, in certain instances, the initial level of TWEAK will forecast the prognosis of the individual. For example, the prognosis can be surgery, development of a category or clinical subtype of IBS, development of one or more symptoms, or recovery from the disease.

In certain other instances, the method further comprises sending the results from the classification to a clinician, e.g., a gastroenterologist or a general practitioner. In yet other instances, the method further provides a diagnosis in the form of a probability that the individual has IBS or a non-IBS intestinal disorder. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having IBS. After IBS is identified, the method can distinguish IBS-A, IBS-C, IBS-D, IBS-M, or IBS-PI. The method can further comprise administering to the individual a therapeutically effective amount of a drug useful for treating IBS-A, IBS-C, IBS-D, IBS-M, or IBS-PI. Suitable drugs include, but are not limited to, tegaserod (Zelnorm™), alosetron (Lotronex®), lubiprostone (Amitiza™), rifamixin (Xifaxan™), MD-1100, probiotics, and a combination thereof.

In instances where the sample is classified as an IBS-A or IBS-C sample and/or the individual is diagnosed with IBS-A or IBS-C, a therapeutically effective dose of tegaserod or other 5-HT$_4$ agonist (e.g., mosapride, renzapride, AG1-001, etc.) can be administered to the individual. In some instances, when the sample is classified as IBS-C and/or the individual is diagnosed with IBS-C, a therapeutically effective amount of lubiprostone or other chloride channel activator, rifamixin or other antibiotic capable of controlling intestinal bacterial overgrowth, MD-1100 or other guanylate cyclase agonist, asimadoline or other opioid agonist, or talnetant or other neurokinin antagonist can be administered to the individual. In other instances, when the sample is classified as IBS-D and/or the individual is diagnosed with IBS-D, a therapeutically effective amount of alosetron or other 5-HT$_3$ antagonist (e.g., ramosetron, DDP-225, etc.), crofelemer or other chloride channel blocker, talnetant or other neurokinin antagonist (e.g., saredutant, etc.), or an antidepressant such as a tricyclic antidepressant can be administered to the individual.

In certain instances, once a sample from an individual has been classified as an IBS sample, the methods of the present invention can further comprise administering to the individual a therapeutically effective amount of a drug useful for treating one or more symptoms associated with IBS (i.e., an IBS drug). For therapeutic applications, the IBS drug can be administered alone or co-administered in combination with one or more additional IBS drugs and/or one or more drugs that reduce the side-effects associated with the IBS drug.

IBS drugs can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra joint, parenteral, intra-arteriole, intradermal, intraventricular, intracranial, intraperitoneal, intralesional, intranasal, rectal, vaginal, or by inhalation. By "co-administer" it is meant that an IBS drug is administered at the same time, just prior to, or just after the administration of a second drug (e.g., another IBS drug, a drug useful for reducing the side-effects of the IBS drug, etc.).

A therapeutically effective amount of an IBS drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an IBS drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the IBS drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

In some embodiments, the therapeutically effective dose takes the form of a pill, tablet, or capsule, and thus, the dosage form can contain, along with an IBS drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An IBS drug can also be formulated into a suppository disposed, for example, in a polyethylene glycol (PEG) carrier.

Liquid dosage forms can be prepared by dissolving or dispersing an IBS drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBS drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBS drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of IBS, an IBS drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBS symptoms, and the IBS drug being employed. For example, dosages can be empirically determined considering the severity of IBS symptoms in an individual classified as having IBS according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular IBS drug in an individual. Determination of the proper dosage for a particular situation is within the skill of the practitioner. Generally, treatment is initiated with smaller dosages which are less than the optimum dose of the IBS drug. Thereafter, the dosage is increased by small increments until the optimum effect under circumstances is reached. For convenience, the total daily dosage may be divided and administered in portions during the day, if desired.

As used herein, the term "IBS drug" includes all pharmaceutically acceptable forms of a drug that is useful for treating one or more symptoms associated with IBS. For example, the IBS drug can be in a racemic or isomeric mixture, a solid complex bound to an ion exchange resin, or the like. In addition, the IBS drug can be in a solvated form. The term "IBS drug" is also intended to include all pharmaceutically acceptable salts, derivatives, and analogs of the IBS drug being described, as well as combinations thereof. For example, the pharmaceutically acceptable salts of an IBS drug include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an IBS drug is suitable for use in the methods of the present invention, e.g., a pharmaceutically acceptable salt of an IBS drug, a free base of an IBS drug, or a mixture thereof.

Suitable drugs that are useful for treating one or more symptoms associated with IBS include, but are not limited to, serotonergic agents, antidepressants, chloride channel activators, chloride channel blockers, guanylate cyclase agonists, antibiotics, opioids, neurokinin antagonists, antispasmodic or anticholinergic agents, belladonna alkaloids, barbiturates, glucagon-like peptide-1 (GLP-1) analogs, corticotropin releasing factor (CRF) antagonists, probiotics, free bases thereof, pharmaceutically acceptable salts thereof, derivatives thereof, analogs thereof, and combinations thereof. Other IBS drugs include bulking agents, dopamine antagonists, carminatives, tranquilizers, dextofisopam, phenytoin, timolol, and diltiazem.

Serotonergic agents are useful for the treatment of IBS symptoms such as constipation, diarrhea, and/or alternating constipation and diarrhea. Non-limiting examples of serotonergic agents are described in Cash et al., *Aliment. Pharmacol. Ther.*, 22:1047-1060 (2005), and include 5-$HT_3$ receptor agonists (e.g., MKC-733, etc.), 5-$HT_4$ receptor agonists (e.g., tegaserod (Zelnorm™), prucalopride, AG1-001, etc.), 5-$HT_3$ receptor antagonists (e.g., alosetron (Lotronex®), cilansetron, ondansetron, granisetron, dolasetron, ramosetron, palonosetron, E-3620, DDP-225, DDP-733, etc.), mixed 5-$HT_3$ receptor antagonists/5-$HT_4$ receptor agonists (e.g., cisapride, mosapride, renzapride, etc.), free bases thereof, pharmaceutically acceptable salts thereof, derivatives thereof, analogs thereof, and combinations thereof. Additionally, amino acids like glutamine and glutamic acid which regulate intestinal permeability by affecting neuronal or glial cell signaling can be administered to treat patients with IBS.

Antidepressants such as selective serotonin reuptake inhibitor (SSRI) or tricyclic antidepressants are particularly useful for the treatment of IBS symptoms such as abdominal pain, constipation, and/or diarrhea. Non-limiting examples of SSRI antidepressants include citalopram, fluvoxamine, paroxetine, fluoxetine, sertraline, free bases thereof, pharmaceutically acceptable salts thereof, derivatives thereof, analogs thereof, and combinations thereof. Examples of tricyclic antidepressants include, but are not limited to, desipramine, nortriptyline, protriptyline, amitriptyline, clomipramine, doxepin, imipramine, trimipramine, maprotiline, amoxapine, clomipramine, free bases thereof, pharmaceutically acceptable salts thereof, derivatives thereof, analogs thereof, and combinations thereof.

Chloride channel activators are useful for the treatment of IBS symptoms such as constipation. A non-limiting example of a chloride channel activator is lubiprostone (Amitiza™), a free base thereof, a pharmaceutically acceptable salt thereof, a derivative thereof, or an analog thereof. In addition, chloride channel blockers such as crofelemer are useful for the treatment of IBS symptoms such as diarrhea. Guanylate cyclase agonists such as MD-1100 are useful for the treatment of constipation associated with IBS (see, e.g., Bryant et al., *Gastroenterol.*, 128:A-257 (2005)). Antibiotics such as neomycin can also be suitable for use in treating constipation associated with IBS (see, e.g., Park et al., *Gastroenterol.*, 128:A-258 (2005)). Non-absorbable antibiotics like rifaximin (Xifaxan™) are suitable to treat small bowel bacterial overgrowth and/or constipation associated with IBS (see, e.g., Sharara et al., *Am. J. Gastroenterol.*, 101:326-333 (2006)).

Opioids such as kappa opioids (e.g., asimadoline) may be useful for treating pain and/or constipation associated with IBS. Neurokinin (NK) antagonists such as talnetant, saredutant, and other NK2 and/or NK3 antagonists may be useful for treating IBS symptoms such as oversensitivity of the muscles in the colon, constipation, and/or diarrhea. Antispasmodic or anticholinergic agents such as dicyclomine may be useful for treating IBS symptoms such as spasms in the muscles of the gut and bladder. Other antispasmodic or anticholinergic agents such as belladonna alkaloids (e.g., atropine, scopolamine, hyoscyamine, etc.) can be used in combination with barbiturates such as phenobarbital to reduce bowel spasms associated with IBS. GLP-1 analogs such as GTP-010 may be useful for treating IBS symptoms such as constipation. CRF antagonists such as astressin and probiotics such as VSL#3® may be useful for treating one or more IBS symptoms. One skilled in the art will know of additional IBS drugs currently in use or in development that are suitable for treating one or more symptoms associated with IBS.

In still another embodiment, the present invention provides a method for monitoring drug efficacy in an individual receiving a drug useful for treating an intestinal disorder (e.g., IBS), comprising:
  (a) determining the presence or level of TWEAK in a first sample from the individual prior to drug treatment;
  (b) determining the presence or level of TWEAK in a second sample from the individual after drug treatment has begun; and
  (c) determining the effectiveness of the drug based upon the presence or level of TWEAK in the first and second samples.

An individual can also be monitored at periodic time intervals to assess the efficacy of a certain therapeutic regimen once a sample from the individual has been classified as a particular intestinal disorder sample. For example, the presence or level of certain markers such as TWEAK may change based on the therapeutic effect of a treatment such as a drug. Patient can be monitored for TWEAK levels to assess response and understand the effects of certain drugs or treatments in an individualized approach. Additionally, patients may not respond to a drug, but their TWEAK levels may change, suggesting that these patients belong to a special population (not responsive) that can be identified by their TWEAK levels. These patients can be discontinued on their current therapy and alternative treatments prescribed.

VII. Example

The following example is offered to illustrate, but not to limit, the claimed invention.

Example 1

TWEAK Discriminates Between IBS and Non-IBS Patient Samples

This example illustrates that determining the presence or level of TWEAK is useful for classifying a patient sample as an IBS sample, e.g., by ruling in IBS. In particular, quartile analysis reveals that TWEAK advantageously discriminates between IBS and non-IBS (i.e., Crohn's disease (CD), ulcerative colitis (UC), GI control, or normal) patient samples. FIG. 1 shows a quartile analysis of TWEAK levels in IBS and non-IBS patient samples. As FIG. 1 illustrates, IBS patient samples have significantly elevated TWEAK levels (median TWEAK level of about 600 pg/ml) compared to non-IBS patient samples.

It is understood that the examples and embodiments described herein are for illustrative purposes only and that various modifications and changes in light thereof will be suggested to persons skilled in the art and are to be included within the purview of this application and are considered to be within the scope of the appended claims. All publications, patents, patent applications, and Genbank Accession Nos. cited herein are hereby incorporated by reference in their entirety for all purposes.

---

What is claimed is:

1. A method for classifying whether a sample from an individual is associated with irritable bowel syndrome (IBS), said method comprising:
   (a) contacting the sample from the individual with a labeled anti-TNF-related weak inducer of apoptosis (TWEAK) antibody under conditions suitable to form a labeled complex of TWEAK antigen and anti-TWEAK antibody;
   (b) detecting the level of TWEAK in the sample from the individual;
   (c) comparing the level of TWEAK in the sample from the individual to the level of TWEAK in a control sample; and
   (d) associating the sample from the individual with IBS when the level of TWEAK in the sample from the individual is elevated compared to the level of TWEAK in the control sample.

2. The method of claim 1, wherein said sample is selected from the group consisting of serum, plasma, whole blood, and stool.

3. The method of claim 1, wherein the level of TWEAK is determined using an enzyme-linked immunosorbent assay (ELISA).

4. The method of claim 1, wherein associating said sample with an intestinal disorder IBS is accomplished using a statistical algorithm.

5. The method of claim 4, wherein said statistical algorithm is a learning statistical classifier system.

6. The method of claim 1, wherein said method further comprises sending the results from said association to a clinician.

7. The method of claim 1, wherein said method further comprises administering to said individual a therapeutically effective amount of a drug useful for treating one or more symptoms associated with IBS.

8. The method of claim 1, wherein said method further provides a diagnosis in the form of a probability that said individual has IBS-A, IBS-C, IBS-D, IBS-M, or IBS-PI.

9. The method of claim 8, wherein said method further comprises administering to said individual a therapeutically effective amount of a drug useful for treating IBS-A, IBS-C, IBS-D, IBS-M, or IBS-PI.

10. The method of claim 1, wherein said method further comprises ruling out intestinal inflammation.

11. A method for monitoring the progression or regression of irritable bowel syndrome (IBS) in an individual, said method comprising:
   (a) contacting a sample from the individual with a labeled anti-TNF-related weak inducer of apoptosis (TWEAK) antibody under conditions suitable to form a labeled complex of TWEAK antigen and anti-TWEAK antibody;
   (b) detecting the level of the labeled complex in the sample from the individual, thereby determining the level of TWEAK in the sample from said individual;
   (c) comparing the level of TWEAK in the sample from the individual to the level of TWEAK in a control sample; and
   (d) determining the severity of the IBS in said individual based upon the level of TWEAK in the sample from the individual.

12. The method of claim 11, wherein said sample is selected from the group consisting of serum, plasma, whole blood, and stool.

13. The method of claim 11, wherein the level of TWEAK is determined using an enzyme-linked immunosorbent assay (ELISA).

14. The method of claim 11, wherein determining the severity of the IBS is accomplished using a statistical algorithm.

15. The method of claim 14, wherein said statistical algorithm is a learning statistical classifier system.

16. The method of claim 11, wherein said method further comprises comparing the severity of the IBS determined in step (b) to the severity of the IBS in said individual at an earlier time.

17. A method for monitoring drug efficacy in an individual receiving a drug useful for treating irritable bowel syndrome (IBS), said method comprising:
   (a) contacting a first sample from the individual prior to drug treatment with a labeled anti-TNF-related weak inducer of apoptosis (TWEAK) antibody under conditions suitable to form a labeled complex of TWEAK antigen and anti-TWEAK antibody in the first sample;
   (b) detecting the level of the labeled complex in the first sample, thereby determining the level of TWEAK in the sample from the individual; determining the level of TWEAK in the first sample from said individual prior to drug treatment;
   (c) contacting a second sample from the individual after drug treatment has begun with the anti-TWEAK antibody under conditions suitable to form a labeled complex of TWEAK antigen and anti-TWEAK antibody in the second sample;
   (d) detecting the level of the labeled complex in the second sample, thereby determining the level of TWEAK in the second sample from said individual after drug treatment has begun; and (e) determining the effectiveness of the drug based upon the level of TWEAK in said first and second samples.

18. The method of claim 17, wherein said first and second samples are independently selected from the group consisting of serum, plasma, whole blood, and stool.

19. The method of claim 17, wherein determining the effectiveness of the drug is accomplished using a statistical algorithm.

20. The method of claim 19, wherein said statistical algorithm is a learning statistical classifier system.

21. The method of claim 17, wherein the effectiveness of the drug is determined by comparing the level of TWEAK in said first sample to the level of TWEAK in said second sample.

\* \* \* \* \*

UNITED STATES PATENT AND TRADEMARK OFFICE
CERTIFICATE OF CORRECTION

| | | |
|---|---|---|
| PATENT NO. | : 8,685,741 B1 | Page 1 of 1 |
| APPLICATION NO. | : 12/043082 | |
| DATED | : April 1, 2014 | |
| INVENTOR(S) | : Lois | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 982 days.

Signed and Sealed this
Twenty-first Day of July, 2015

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 249
<212> TYPE: PRT
<213> ORGANISM: Homo sapiens
<220> FEATURE:
<223> OTHER INFORMATION: tumor necrosis factor (ligand) superfamily
      member 12 (TNFSF12), TNF-related weak inducer of apoptosis
      (TWEAK), APO3 ligand (APO3L), DR3 ligand (DR3LG), fibroblast
      growth factor-inducible 14 (Fn14) ligand, UNQ181/PRO207

<400> SEQUENCE: 1

Met Ala Ala Arg Arg Ser Gln Arg Arg Arg Gly Arg Arg Gly Glu Pro
 1               5                  10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
 65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205
```

```
Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245
```

<210> SEQ ID NO 2
<211> LENGTH: 1407
<212> TYPE: DNA
<213> ORGANISM: Homo sapiens
<220> FEATURE:
<223> OTHER INFORMATION: tumor necrosis factor (ligand) superfamily
      member 12 (TNFSF12), TNF-related weak inducer of apoptosis
      (TWEAK), APO3 ligand (APO3L), DR3 ligand (DR3LG), fibroblast
      growth factor-inducible 14 (Fn14) ligand, UNQ181/PRO207, MGC20669,
      MGC129581 cDNA

<400> SEQUENCE: 2

```
ctctccccgg cccgatccgc ccgccggctc ccctcccccc gatccctcgg gtcccgggat    60 ggggggggcgg tgaggcaggc acagccccccc gcccccatgg ccgcccgtcg gagccagagg   120 cggaggggggc gccgggggga gccgggcacc gccctgctgg tcccgctcgc gctgggcctg   180
ggcctggcgc tggcctgcct cggcctcctg ctggccgtgg tcagtttggg gagccgggca   240
tcgctgtccg cccaggagcc tgcccaggag gagctggtgg cagaggagga ccaggacccg   300
tcggaactga atccccagac agaagaaagc caggatcctg cgcctttcct gaaccgacta   360
gttcggcctc gcagaagtgc acctaaaggc cggaaaacac gggctcgaag agcgatcgca   420
gcccattatg aagttcatcc acgacctgga caggacgagc gcaggcagg tgtggacggg   480 acagtgagtg gctgggagga agccagaatc aacagctcca gccctctgcg ctacaaccgc   540
cagatcgggg agtttatagt cacccgggct gggctctact acctgtactg tcaggtgcac   600
tttgatgagg ggaaggctgt ctacctgaag ctggacttgc tggtggatgg tgtgctggcc   660
ctgcgctgcc tggaggaatt ctcagccact gcggcgagtt ccctcgggcc ccagctccgc   720
ctctgccagg tgtctgggct gttggccctg cggccaggt cctccctgcg gatccgcacc   780
ctcccctggg cccatctcaa ggctgccccc ttcctcacct acttcggact cttccaggtt   840
cactgagggg ccctggtctc cccgcagtcg tcccaggctg ccggctcccc tcgacagctc   900
tctgggcacc cggtcccctc tgccccaccc tcagccgctc tttgctccag acctgcccct   960
ccctctagag gctgcctggg cctgttcacg tgttttccat cccacataaa tacagtattc  1020
ccactcttat cttacaactc ccccaccgcc cactctccac ctcactagct ccccaatccc  1080 tgacccttg aggcccccag tgatctcgac tcccccctgg ccacagaccc cagggcatt   1140 gtgttcactg tactctgtgg gcaaggatgg gtccagaaga ccccacttca ggcactaaga  1200
ggggctggac ctggcggcag gaagccaaag agactgggcc taggccagga gttcccaaat  1260
gtgaggggcg agaaacaaga caagctcctc ccttgagaat tccctgtgga ttttaaaac  1320 agatattatt tttattatta ttgtgacaaa atgttgataa atggatatta aatagaataa  1380
gtcataaaaa aaaaaaaaa aaaaaaa                                       1407
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:synthetic
      RT-PCR TWEAK sense primer -continued

```
<400> SEQUENCE: 3
cccatggccg cccgtcggag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:synthetic
      RT-PCR TWEAK antisense primer

<400> SEQUENCE: 4
gggccaacag cccagacacc                                              20
```